US00PP24535P3

(12) United States Plant Patent
Pavlich

(10) Patent No.: US PP24,535 P3
(45) Date of Patent: Jun. 10, 2014

(54) *CISTUS* PLANT NAMED 'MCGUIRE'S GOLD'

(50) Latin Name: *Cistus×hybridus*
Varietal Denomination: McGuire's Gold

(76) Inventor: John C. Pavlich, East Olympia, WA (US)

( * ) Notice: Subject to any disclaimer, the term of this patent is extended or adjusted under 35 U.S.C. 154(b) by 183 days.

(21) Appl. No.: 13/506,432

(22) Filed: Apr. 17, 2012

(65) Prior Publication Data

US 2013/0276184 P1 Oct. 17, 2013

(51) Int. Cl.
*A01H 5/00* (2006.01)

(52) U.S. Cl.
USPC ..... Plt./226; Plt./263.1

(58) Field of Classification Search
USPC ..... Plt./226, 263.1
See application file for complete search history.

*Primary Examiner* — June Hwu
*Assistant Examiner* — Louanne Krawczewicz Myers
(74) *Attorney, Agent, or Firm* — Klarquist Sparkman, LLP

(57) ABSTRACT

A new and distinct form of *Cistus* plant characterized by gold leaves, a low, mounding habit, and excellent vigor.

1 Drawing Sheet

Botanical denomination: *Cistus×hybridus*.
Variety designation: 'McGuire's Gold'.

BACKGROUND OF THE INVENTION

The present invention relates to a new and distinct cultivar of *Cistus×hybridus*, given the name, 'McGuire's Gold'. *Cistus* is in the family *Cistaceae*. This gold leaf cultivar was found as a branch mutation of *Cistus×hybridus* 'Mickie', U.S. Plant Pat. No. 23,024. This mutation was found at the home of the inventor in a cultivated area in Olympia, Wash. It is the only all gold leaf *Cistus* known to the inventor.

Compared to *Cistus×hybridus* 'Mickie', the new cultivar has all gold rather than variegated gold and green leaves.

Compared to *Cistus×hybridus*, an unpatented plant, the new cultivar has all gold rather than all green leaves.

*Cistus* 'McGuire's Gold' is uniquely distinguished by:

1. all gold leaves,
2. a low, mounding habit,
3. and excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a greenhouse-grown two-year-old *Cistus* 'McGuire's Gold' with a flower growing in a two gallon container in May in Canby, Oreg.

DETAILED PLANT DESCRIPTION

The following is a detailed description of the new *Cistus* cultivar based on observations of a two-year-old specimen grown outside in five gallon containers in Canby, Oreg. in mid-June. The color descriptions are all based on The Royal Horticultural Society Colour Chart, 5$^{th}$ edition.

Plant:

*Type*.—Evergreen shrub.
*Form*.—Low, mounding.
*Cold hardiness*.—USDA Zone 7-10.
*Size*.—Grows to 81 cm wide and 28 cm high.
*Vigor*.—Excellent.
*Stem*.—Grows to 59 cm long and to 18 mm wide at the base, woody, with internodes 2 cm to 4 cm long, Brown 200A.
*Rooting*.—Plants root easily from soft wood cuttings.

Leaf:

*Type*.—Simple.
*Arrangement*.—Opposite.
*Shape*.—Ovate.
*Venation*.—Pinnate.
*Margins*.—Slightly undulate, entire.
*Apex*.—Acute.
*Base*.—Truncate.
*Blade size*.—Grows to 4.7 cm long and 2.2 cm wide.
*Surface texture*.—Rugose, pubescent on both sides.
*Petiole*.—Grows to 15 mm long and 1 mm wide, pubescent, Yellow Green 146C with slight tints of Greyed Purple 187B on top side when grown in full sun.
*Leaf color*.—Brightest when grown in a full day of summer sun, topside Yellow 11A darkening to 11B with age; bottom side Yellow Green N144A; fall and winter top and bottom sides Yellow Green N144A on newest growth to Yellow Green 146B on older leaves.
*Leaf fragrance*.—None.

Inflorescence:

*Type*.—Usually two, cymose, at axillary nodes on branch tips.
*Peduncle*.—Grows to 5.5 cm long and 1 mm wide, pubescent, Yellow Green 144A.
*Pedicel*.—About 9 mm long and 1 mm wide, pubescent, Yellow Green 144A.
*Bloom period*.—June in Canby, Oreg.

Flower bud:

*Size.*—12 mm long and 5 mm wide at the widest point prior to opening.

*Description.*—Ovoid.

*Surface texture.*—Pubescent.

*Color.*—Yellow Green 145D strongly tinted Greyed Purple 187B.

Flower:

*Type.*—Actinomorphic.

*Shape.*—Rotate, cup shaped.

*Size.*—Grows to 35 mm wide and 6 mm deep.

*Corolla description.*—5 petals, each 2 cm long and 17 mm wide, flabellate in shape, margin entire, tip premorse to retuse, base cuneate, both sides glabrous and White NN155A with Yellow 12A at the very base.

*Calyx description.*—5 sepals, each grow to 9 mm long and 5 mm wide, ovate, tips acuminate, base cordate, margin entire, pubescent outside, glabrous inside, Yellow 11D with edges Greyed Purple 187B on both sides.

*Pistil description.*—1, 3 mm long and 2 mm wide, ovary 1 mm long and 2 mm wide, pubescent and Yellow Green 145B; style less than 1 mm long, Yellow Green 145B, stigma globose, 2 mm long and 2 mm wide, Yellow 11D.

*Stamen description.*—Numerous (usually about 100) and showy, filaments 3.5 mm long and Yellow 13A, anthers less than 1 mm long and Yellow Orange 23A, pollen Yellow Orange 23A.

*Fragrance.*—Slight.

*Lastingness.*—A flower lasts about 1 day.

Fruit and seed: None, sterile.

Pests and diseases: No particular pest or disease problems or resistance has been observed.

I claim:

1. A new and distinct form of *Cistus* plant substantially as shown and described.

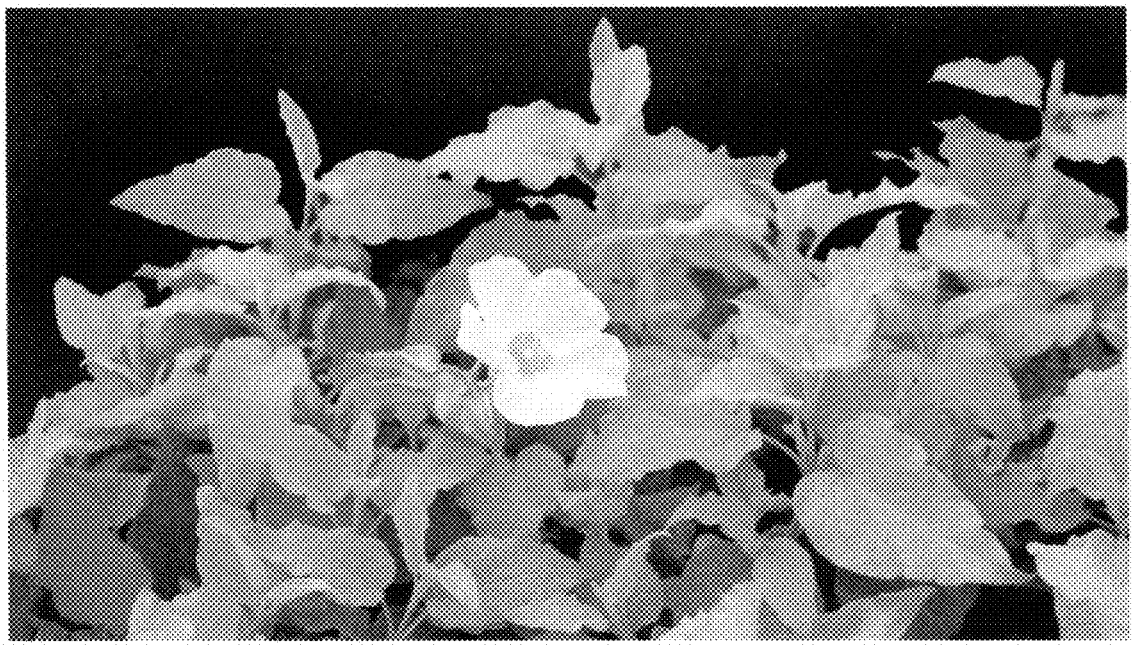

* * * * *